United States Patent [19]

Wu

[11] Patent Number: 5,569,680

[45] Date of Patent: Oct. 29, 1996

[54] METHOD OF TREATING INFLAMMATORY BOWEL DISEASE WITH TRIBUTYRIN

[75] Inventor: Gary D. Wu, Ardmore, Pa.

[73] Assignee: Trustees of the Univ. of Penna

[21] Appl. No.: 387,116

[22] Filed: Feb. 13, 1995

[51] Int. Cl.⁶ .................... A61K 31/215; C07C 69/003
[52] U.S. Cl. ................. 514/786; 554/30; 554/174
[58] Field of Search .................. 514/786; 536/4.1; 554/30, 174

[56] References Cited

U.S. PATENT DOCUMENTS

| | | | |
|---|---|---|---|
| 5,084,481 | 1/1992 | Ulrich et al. | 514/557 |
| 5,110,814 | 5/1992 | Engel et al. | 514/212 |

OTHER PUBLICATIONS

Scheppach et al. Gastroenterology 103:51–56, 1992.
Steinhart et al. Am. J. Gastro. 89:179–183, 1994.
Deschner et al. Cancer Letters 52:79–82, 1990.
Biasco et al., "Proliferative and Antigenic Properties of Rectal Cells in Patients with Chronic Ulcerative Colitis", *Cancer Res.* (1984), 44:5450–5454.
Breuer et al., "Rectal Irrigation with Short–Chain Fatty Acids for Distal Ulcerative Colitis", *Dig. Dis. Sci.* (1991), 36:185–187.
Che, Z. and Breitman, T. R., "Tributyrin: A Prodrug of Butyric Acid for Potential Clinical Application in Differentiation Therapy", *Cancer Research* (1994), 54:3494–3499.
Chomczynski, P. and Sacchi, N., "Single–Step Method of RNA Isolation by Acid Guanidinium Thiocyanate–Phenol–Chloroform Extraction", *Anal. Biochem.* (1987) 162:156–159.
Cummings, J. H., "Fermentation in the Human Large Intestine: Evidence and Implications for Health", *Lancet* (1983), 1:1206–1209.
Deschner et al., "Dietary butyrate (tributyrin) does not enhance AOM–induced colon tumorigenesis", *Cancer Letters* (1990), 52:79–82.
Glotzer et al., "Proctitis and Colitis Following Diversion of the Fecal Stream," *Gastroenterology* (1981) 80:438–441.
Harig et al., "Treatment of Diversion Colitis with Short–Chain–Farry Acid Irrigation", *N. Engl. J. Med.* (1989), 320:23–28.
Huang et al. "Overexpression of a Truncated Growth Hormone Receptor in the Sex–Linked Dwarf Chicken: Evidence for a Splice Mutation", *Mol. Endo.* (1993), 7:1391–1398.
Kripke et al., "Experimental short–bowel syndrome: effect of an elemental diet supplemented with short–chain triglycerides", *Am. J. Clin. Nutr.* (1991), 53:954–962.
Marchuk et al., "Construction of T–vectors, a rapid and general system for direct cloning of unmodified PCR products", *Nuc. Acids Res.* (1991), 19:1154.
Nudelman et al., "Novel Anticancer Prodrugs of Butyric Acid", *J. Med. Chem.* (1992), 35(4):687–694.
Planchon et al., "Differential Elimination of Synthetic Butyric Triglycerides In Vivo: A Pharacokinetic Study", *J. Pharm. Sci.* (1993), 82:1046–1048.

Robertson et al., "Dietary Nonprotein Calories and Cerebral Infarction Size in Rats", *Stroke* (1992), 23:564–568.
Risio, M., "Cell Proliferation in Colorectal Tumor Progression: An Immunohistochemical Approach to Intermediate Biomarkers", *J. Cell Biochem.* (1992), 16G:79–87.
Roediger, W., "Role of Anaerobic Bacteria in the Metabloic Welfare of the Colonic Mucosa in Man," *Gut* (1980) 21:793–798.
Roediger, W., "Utilization of Nutrients by Isolated Epithelial Cells of the Rat Colon," *Gastroenterology* (1982) 83:424–429.
Roediger, W., "The Starved Colon—Diminished Mucosal Nutrition, Diminished Absorption, and Colitis", *Dis. Col. and Rectum* (1990), 33:858–862.
Roediger, W., "The Colonic Epithelium in Ulcerative Colitis: An Energy–Deficient Disease", *Lancet* (1980), 2:712–715.
Serafini et al., "Rate and pattern of epithelial cell proliferation in ulcerative colitis," *Gut* (1981), 22:648–652.
Scheppach et al., "Effect of Butyrate Enemas on the Colonic Mucosa in Distal Ulcerative Colitis," *Gastroenterology* (1992), 103:51–56.
Steinhart et al., "Treatment of Refractory Ulcerative Proctosigmoiditis with Butyrate Enemas", *Am. J. Gastro.* (1994), 89:179–183.
Snyderman et al., "The Absorption of Short–Chain Fats By Premature Infants", *Arch Dis. Child.* (1955), 30:83–84.
Schweinfest et al., "Identification of a colon mucosa gene that is down–regulated in colon adenomas and adenocarcinomas", *Proc. Natl. Acad. Sci. USA* (1993), 90:4166–4170.
Traber et al., "Sucrase–isomaltase gene expression along crypt–villus axis of human small intestine is regulated at level of mRNA abundance", *Mol. Cell. Biol.* 12:3614–3627.
Traber et al., "Novel DNA–Binding Proteins Regulate Intestine–Specific Transcription of the Scurase–Isomaltase Gene", *Am. J. Physiol.* (1992), 262:G123–G130.
Vernia et al., "Organic Anions and the Diarrhea of Inflammatory Bowel Disease", *Dig. Dis. Sci.* (1988), 33:1353–1358.
Wu et al., "Isolation and Characterization of the Human Sucrase–Isomaltase Gene and Demonstrationl of Intestine–Specific Transcriptional Elements," *J. Biol. Chem.* 267:7863–7870.
Wu et al., "Sucrase–Isomaltase Gene Expression in Barrett's Esophagus and Adenocarcinoma", *Gastroenterology* (1993), 105:837–844.
Yu et al., "The assessment of cellular proliferation by immunohistochemistry: a review of currently available methods and their applications", *Histochemical Journal* (1992), 24:121–131.

*Primary Examiner*—Gary L. Kunz
*Attorney, Agent, or Firm*—Law Offices of Jane Massey Licata

[57] ABSTRACT

A method for treating inflammatory bowel disease in a patient by inhibiting the production of interleukin-8 in intestinal epithelial cells by administering to said patient an enema of an effective amount of tributyrin.

1 Claim, 1 Drawing Sheet

METHOD OF TREATING INFLAMMATORY BOWEL DISEASE WITH TRIBUTYRIN

BACKGROUND OF THE INVENTION

Short chain fatty acids (SCFA) are normal products of anaerobic bacterial fermentation of carbohydrates in the colon and are the major energy source for the colonic epithelium. Approximately 90% of the total SCFA content in the colon is composed of acetic, propionic, and n-butyric acids. Cummings, J. H. *Lancet* (1983) 1:1206–1209; Roediger, W. *Gut* (1980) 21:793–798; Roediger, W. *Gastroenterology* (1982) 83:424–429. It has been suggested that a lack of luminal SCFAs leads to mucosal atrophy in the short term and nutritional colitis after prolonged periods. Roediger, W. *Dis. Col. and Rectum* (1990) 33:858–862. This is particularly evident in diversion colitis which develops after diversion of the fecal stream and resolves with restoration of colorectal continuity. Glotzer et al. *Gastroenterology* (1981) 80:438–441. SCFA enemas have been shown to be effective in the treatment of diversion colitis. Harig et al. *N. Engl. J. Med.* (1989) 320:23–28.

It is not known whether or not ulcerative colitis has the same cause as diversion colitis. While some investigators have shown that SCFA levels are decreased in the stool of patients with ulcerative colitis (Vernia et al. *Dig. Dis. Sci.* (1988) 33:1353–1358) and that mitochondrial fatty acid oxidation is abnormal in colon cells isolated from patients with active disease (Roediger, W. *Lancet* (1980) 2:712–715), it is not known whether these alterations are responsible for or a result of active ulcerative colitis. The histologic appearance of active ulcerative colitis includes an intense lymphoplasmocytosis limited to the mucosa and submucosa often notable for a neutrophilic infiltrate invading the colonic epithelium, referred to as a crypt abscess. Ulcerative colitis may be, therefore, classified as a disorder of the colonic mucosa. Several investigators have shown that the colonic epithelium is in a hyperproliferative state with the expansion of the proliferative compartment from the lower crypt to the upper crypt extending to the surface epithelium of the colon. Biasco et al. *Cancer Res.* (1984) 44:5450–5454; Serafini et al. *Gut* (1981) 22:648–652. This proliferative state is independent of the degree of inflammation as well as the duration of disease and exists even when the disease is in a quiescent state. These findings suggest an intrinsic abnormality of the colonic epithelium in ulcerative colitis. Similar hyperproliferative states have been observed in patients at risk for colonic malignancy such as in familial polyposis coli, sporadic colon adenomas and familial nonpolyposis colon cancer. Risio, M. *J. Cell Biochem.* (1992) 16G:79–87.

Butyrate enemas have been used to reduce inflammation in patients with distal ulcerative colitis. Breuer et al. *Dig. Dis. Sci.* (1991) 36:185–187; Scheppach et al. *Gastroenterology* (1992) 103:51–56; Steinhart et al. *Am. J. Gastro.* (1994) 89:179–183. In two studies, butyrate enemas were shown to result in a significant clinical response in patients whose disease did not respond to traditional forms of treatment including use of corticosteroids and 5-amino salicylic acid compounds. The basis of this response is unknown. Scheppach et al. observed that the labeling index of clonocytes in the upper crypt of patients with ulcerative colitis fell to that of normal healthy controls after treatment with butyrate enemas. Irrigation of the colon with short chain fatty acids also resulted in improvement in patients with diversion colitis. However, the use of butyrate enemas in these diseases is severely limited due to its extremely strong odor which leads to patients refusing to continue treatment.

Butyric acid has also been shown to induce cytodifferentiation in vitro of a wide variety of neoplastic cells. Chen, Z. and Breitman, T. R. *Cancer Research* (1994) 54:3494–3499. The potential clinical utility of butyric acid, however, is limited by the apparent difficulty of achieving effective concentrations because of rapid metabolism and short plasma half-life. Results in such studies have been variable. For examples, butyric acid, 500 mg/kg body weight per day, as the sodium salt, was given parenterally to a child with acute myelogenous leukemia and induced partial remission. However, sodium butyrate provided at 1% to 2% in the drinking water enhanced development of colonic neoplasia in 1,2-dimethylhydrazine-initiated rats. In further studies Deschner et al. demonstrated dietary butyrate in the form of tributyrin was non-toxic when fed at the 5% level, allowing for normal weight gain and good health. *Cancer Letters* (1990) 52:79–82. The dietary butyrate in this study did not enhance colonic neoplasia, however, the tributyrate also did not exert a significant protective effect against chemically induced colonic neoplasia.

Chen and Breitman suggest use of tributyrin as a prodrug for butyric acid either as a sole agent or in combination with other agents, for cytodifferentiation therapy of human leukemia and other malignancies. *Cancer Research* (1994) 54:3494–3499. Diets high in short chain triglycerides such as triacetin and tributyrin have been demonstrated to enhance colonic mucosal adaptation and significantly increase jejunal mucosal mass as compared with chemically defined diets containing equivalent calories in the form of carbohydrate or medium chain triglycerides in rats with surgically created short-bowel syndrome. Kripke et al. *Am. J. Clin. Nutr.* (1991) 53:954–62. From these studies it was suggested that short chain triglycerides may be a useful new enteral fuel in patients with short-bowel syndrome or other disorders of fat absorption in which medium chain triglycerides represent the current standard of nutritional care. Such diets have also been suggested for patients with neurological injuries to supply systemic caloric and protein requirements without the adverse effects of conventional high glucose diets. Robertson et al. *Stroke* (1992) 23:564–568. However, Nudelman et al. examined a number of possible prodrugs for butyric acid in cytodifferentiation experiments including glyceryl tributyrate and did not find tributyrates to increase efficacy. *J. Med. Chem.* (1992) 35(4):687–694. Glyceryl tributyrate, which is capable of releasing three butyrate units per prodrug molecule and has a lipophilicity similar to methyl butyrate, which was shown to inhibit cell proliferation 90%, was only as active as butyric acid with a maximum inhibition of 35%. This lack of activity of the tributyrate was suggested to be due to lower penetration rates into the cells, slow hydrolysis, or a combination of both factors.

It has now been unexpectedly found that tributyrin can be used therapeutically in the treatment of inflammatory bowel disease.

SUMMARY OF THE INVENTION

An object of the invention is to provide a method of treating inflammatory bowel disease in a patient comprising administration of an effective amount of tributyrin to the patient.

DETAILED DESCRIPTION OF THE INVENTION

Figure 1:
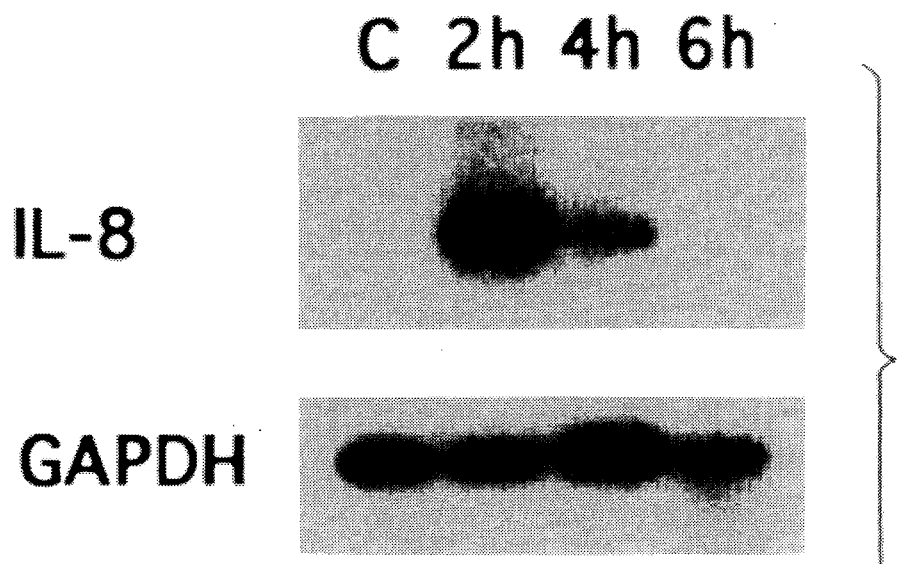
FIG. 1 is a Northern blot of total RNA from Caco-2 cells stimulated with IL-1β which is hybridized with a cDNA probe for IL-8 and then rehybridized with a cDNA probe for glyceraldehydephosphate dehydrogenase (GAPDH) to demonstrate the loading and integrity of the RNA in each lane.

The incidence of inflammatory bowel disease, a term used to designate two chronic inflammatory gastrointestinal disorders, Crohn's disease and ulcerative colitis, is estimated to be between 4% and 10% with 25,000 new cases occurring annually. Crohn's disease is a subacute and chronic inflammation that extends through the intestinal mucosa resulting in the formation of fistulas, fissures and abscesses. Granulomas occur in 50% of the cases. As the disease advances, the intestinal lumen narrows, causing obstruction. Ulcerative colitis, a chronic inflammatory disease of the superficial mucosa of the colon affects approximately 500,000 individuals in the United States alone. This disease is characterized by multiple ulcerations and friability of the colonic mucosa associated with diffuse inflammations. In addition to the morbidity associated with intestinal inflammation, patients with ulcerative colitis for greater than 8 to 10 years duration have a dramatically increased risk for developing colon cancer. Medical treatment for both Crohn's disease and ulcerative colitis, collectively referred to as chronic inflammatory bowel disease, is aimed at reducing inflammation.

Butyrate enemas have been found to be an effective treatment for ulcerative colitis unresponsive to conventional treatment. However, the utility of these enemas is severely limited due to their intensely unpleasant odor which leads to patients refusing to use the treatment. It has now been found that tributyrin, a prodrug of butyrate which does not have an unpleasant odor, is an even more potent inhibitor of epithelial inflammatory response than sodium butyrate. These studies indicate that tributyrin is a more effective and better tolerated anti-inflammatory agent in the treatment of chronic inflammatory bowel disease. Tributyrin was initially synthesized during the 1920's. It is commercially available through a number of chemical distributors including Sigma Chemical Company, St. Louis, Mo. and Aldrich Chemical Company Inc., Milwaukee, Wis. Tributyrin has been traditionally used as an analytical reagent in the study of the enzymatic hydrolysis of triglycerides. More recently tributyrin has been suggested as a possible nutritional agent.

Tributyrin is an ester of butyrate, a short chain fatty acid. Short chain fatty acids are normal products of anaerobic bacterial fermentation of carbohydrates in the colon and are the major source of nutrition for the human colonic epithelium. Butyrate, the short chain fatty acid most avidly metabolized by colonocytes, has recently been demonstrated to be an effective treatment for several intestinal inflammatory diseases including ulcerative colitis and diversion colitis. In these studies, the butyrate was administered as sodium butyrate, a water soluble, polar compound. It has now been found that tributyrin, an apolar and hydrophobic compound, can also penetrate colonic epithelial cells at least as effectively as sodium butyrate, resulting in a 3-fold increase in effect as predicted by the molar ratio of butyrate delivered.

In vitro data demonstrate that sodium butyrate is capable of inducing intestinal epithelial cell differentiation concurrent with inhibiting gene expression for the proinflammatory cytokine IL-8. It has now been found that tributyrin leads to an identical biological response in vitro at concentrations one third (⅓) that of sodium butyrate. These results were unexpected in light of in vitro experiments related to cytodifferentiation wherein it was found that tributyrin was only as effective as sodium butyrate in inhibiting cell proliferation at the same dose. Nudelman et al. *J. Med. Chem.* (1992) 35(4):687–694. Furthermore, these results suggest that colonic epithelial cells contain intracellular esterases that allow tributyrin to be metabolized to butyrate.

No toxicity has been observed in mice treated with tributyrin either orally or intraperitoneally with a dose of 26.5 mmole/kg. Planlchon et al. *J. Pharm. Sci.* (1993) 82:1046–1048. In addition, tributyrin has been well tolerated in humans. For example, no detectable side effects were seen after six premature infants were fed butyrates for 4 days at doses of about 20 mmol/kg/day. Snyderman et al. *Arch Dis. Child.* (1955) 30:83–84.

In the present invention, a method is provided for treating inflammatory bowel disease in a patient which comprises administering to a patient an effective amount of tributyrin. By "effective amount" it is meant a concentration sufficient to inhibit inflammation in the colon associated with this disease. Effective concentrations of tributyrin can be easily determined based upon the data provided in the instant disclosure and knowledge of those of skill in the art. By "patient" it is meant an individual suffering from inflammatory bowel disease.

Treatment of inflammatory bowel disease with tributyrin will be demonstrated in Phase I and Phase II clinical trials. In these studies, tributyrin will be administered as an enema at 25, 50 and 100 mM concentrations. In a preferred embodiment, an aqueous emulsion of tributyrin is prepared in 0.9N saline. A 60 cc tributyrin enema is administered BID with at least a 30 minute retention. Efficacy of the treatment will be determined by endoscopic appearance of the mucosa by flexible sigmoidoscopy before and after treatment with tributyrin. Random biopsies of the colonic mucosa will be obtained during these procedures for histologic analysis. These biopsies will be used to determine the degree of inflammation present. In addition, the biopsies will be used to determine if there is alteration in colonocyte proliferation and/or differentiation by quantitatively scoring the presence of immunohistochemical markers for cell proliferation such as proliferating cell nuclear antigen (PCNA) (Yu et al., *Histochemical Journal* (1992) 24:121–131) and cellular differentiation such as down regulated adenoma (DRA) (Schweinfest et al. *Proc. Natl. Acad. Sci. USA* (1993) 90:4166–4170). The pattern of staining will be referenced to 6 zones that divide the colonic epithelium from the crypt base, the proliferative undifferentiated zone in normal colon, to the surface epithelium, the nonproliferative differentiated zone in normal colon. In addition, clinical symptoms including frequency of bowel movements, sense of well being and the presence or absence of diarrhea, visible blood in the feces, abdominal pain or tenesmus, or fever will be recorded.

The following nonlimiting examples are provided to further illustrate the present invention.

EXAMPLES

Example 1

Induction of IL-8 mRNA in Caco-2 cells

Caco-2 cells (American Type Culture Collection, Rockville, Md.) were plated at a density of $4 \times 10^4$ cells per cm$^2$ in 10 cm dishes containing Dulbecco's modified Eagle's medium (DMEM) with 10% fetal bovine serum and penicillin/streptomycin as described by Wu et al. *J. Biol. Chem.* 267:7863–7870 and Traber et al. *Mol. Cell. Biol.*

12:3614–3627. At day 5 the cells were stimulated with complete medium containing 20 ng/ml of IL-1β (R and D Systems, Minneapolis, Minn.). Total RNA was isolated from these cells 2, 4 and 6 hours after the addition of IL-1β containing medium as well as from a control cell population not treated with IL-1β in accordance with procedures described by Chomczynski, P. and Sacchi, N. *Anal. Biochem.* (1987) 162:156–159. Ten micrograms of RNA for each sample was electrophoretically separated, transferred to a nylon membrane, and UV crosslinked in accordance with procedures described by Traber et al. *Am. J. physiol.* (1992) 262:G123–G130. A cDNA probe for IL-8 was prepared by RT-PCR of total RNA from Caco-2 cells stimulated with IL-1β for 2 hours. Random hexamers were used for reverse transcription of the RNA using reaction conditions similar to those described by Wu et al. *Gastroenterology* (1993) 105:837–844. A 277 bp cDNA was amplified from the RT reaction by PCR using the 5' primer IL-8(+103) and the 3' primer IL-8(EX4), cloned using a TA-vector (Marchuk et al. *Nuc. Acids Res.* (1991) 19:1154), and labeled with $^{32}$P using a Random Primers DNA labeling System (Gibco BRL, Gaithersburg, Md.). Hybridization of the Northern blots were performed using conditions as described by Huang et al. *Mol. Endo.* (1993) 7:1391–1398.

IL-8(+103)  5'-GTGGGATCCATGACTTCCAAGCTG-GCC-3' (SEQ ID NO: 1)

IL-8(EX4)  5'-GTGGGATCCGAATTCTCAGC-CCTCTTC-3' (SEQ ID NO: 2)

GGATCC indicates the BAM HI site.

EXAMPLE 2

Inhibition of IL-1β stimulated IL-8 gene expression with tributyrin

Approximately 18 hours post-plating, Caco-2 cells were placed in complete medium containing various concentrations of tributyrin (Sigma, St. Louis, Mo.) diluted in ethanol (0.1 to 1.0 mM). Caco-2 cells were also plated that were not treated with this compound. The medium was changed on a daily basis for 3 days. On day 5 all the cells (except for control) were stimulated with IL-1β (5 ng/ml) for 2 hours. Total RNA was then isolated and Northern blots performed as described in Example 1. The blots were hybridized to the IL-8 cDNA probe also described in Example 1. Rehybridization of the same blot with a probe for 7S ribosomal RNA demonstrates the loading and integrity of the RNA in each lane.

Figure 2:
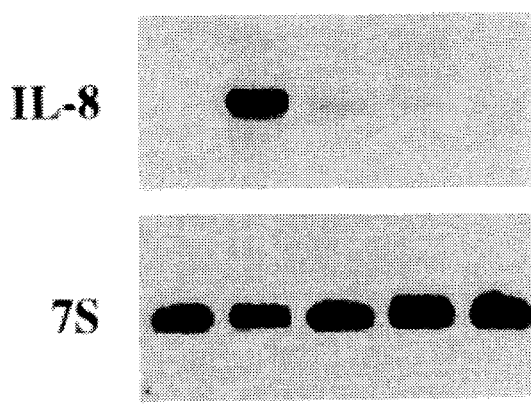
FIG. 2 is a Northern blot measuring IL-8 mRNA levels using RNA isolated from Caco-2 cells treated with tributyrin which is hybridized with a cDNA Probe for IL-8 and then rehybridized with a probe for 7S ribosomal RNA to demonstrate the loading and integrity of the RNA in each lane.

Increasing concentrations of tributyrin from 0.1 to 1.0 mM tributyrin lead to a dose dependent reduction in steady state levels of IL-8 mRNA (see FIG. 2). These concentrations were well tolerated by Caco-2 cells without any evidence of cell death. Treatment of Caco-2 cells at concentration higher that 1.0 mM, which caused significant toxicity and cell death, led to increased expression of IL-8 mRNA.

---

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 27
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 1:

GTGGGATCCA TGACTTCCAA GCTGGCC    27

( 2 ) INFORMATION FOR SEQ ID NO: 2:

( i ) SEQUENCE CHARACTERISTICS:
        ( A ) LENGTH: 27
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 2:

GTGGGATCCG AATTCTCAGC CCTCTTC    27

---

No IL-8 mRNA was detectable in control cells (see FIG. 1). However, following stimulation with IL-1β, there was a dramatic increase of IL-8 mRNA with peak levels at 2 hours which decreased at later time points (see FIG. 1). Rehybridization of the same blot with GAPDH demonstrated the loading and integrity of the RNA in each lane (see FIG. 1).

What is claimed:

1. A method of treating inflammatory bowel disease in a patient by inhibiting the production of interleukin-8 in intestinal epithelial cells by administering to said patient through an enema an effective amount of tributyrin.

\* \* \* \* \*